United States Patent [19]

Paciorek et al.

[11] Patent Number: 5,326,910
[45] Date of Patent: Jul. 5, 1994

[54] MONOPHOSPHA-S-TRIAZINES OF IMPROVED HYDROLYTIC AND THERMAL OXIDATIVE STABILITY

[75] Inventors: Kazimiera J. L. Paciorek, Corona Del Mar; Steven R. Masuda; Wen-Huey Lin, both of Laguna Niguel, all of Calif.

[73] Assignee: Lubricating Specialties Co., Vernon, Calif.

[21] Appl. No.: 24,149

[22] Filed: Mar. 1, 1993

[51] Int. Cl.$^5$ ............................................. C07F 9/6584
[52] U.S. Cl. ..................................................... 564/13
[58] Field of Search ........................................ 564/13

[56] References Cited

U.S. PATENT DOCUMENTS 3,654,273  4/1972  Schuman et al. ............... 544/216
4,166,071  8/1979  Paciorek et al. ................ 564/13

OTHER PUBLICATIONS

March, J. *Advanced Organic Chemistry*; John Wiley and Sons: New York, 1992; pp. 417–418.

*Primary Examiner*—Robert W. Ramsuer
*Assistant Examiner*—Michael Ambrose
*Attorney, Agent, or Firm*—Grant L. Hubbard

[57] ABSTRACT

Hydrolytically and thermooxidatively stable monophospha-s-triazines prepared by reaction of octafluoroisobutylene epoxide with an acid fluoride followed by transformation of the resultant product into an amide, then into a nitrile, reacting the nitrile with ammonia and reacting the imidoylamidine resulting from the previous steps with di-aryltrihalophosphorane to produce mono-phospha-s-triazines that are useful as antioxidant - anticorrosion agents for perfluoroalkylether fluids are disclosed.

5 Claims, No Drawings

MONOPHOSPHA-S-TRIAZINES OF IMPROVED HYDROLYTIC AND THERMAL OXIDATIVE STABILITY

RIGHTS OF THE GOVERNMENT

The invention was made with Government support under Contract No. NAS3-26508 awarded by the National Aeronautics and Space Administration. The Government has certain rights in this invention.

FIELD OF THE INVENTION

The invention relates to monophospha-s-triazines of improved hydrolytic stability.

BACKGROUND OF THE INVENTION

Because of their thermal and oxidative stability and wide fluid ranges perfluoroalkylether fluids are being considered for use as engine oils, hydraulic fluids and greases and are actually used currently in space guidance systems. However, in oxidizing atmospheres and under conditions of boundary lubrications these compositions corrode metals/metal alloys and provide volatile degradation products. Two kinds of additives were found to be effective in arresting the degradation process namely phospha-s-triazines described by K. L. Paciorek, R. H. Kratzer, J. Kaufman and T. I. Ito in U.S. Pat. No. 4,215,072 (1980), and by K. L. Paciorek, R. H. Kratzer, J. Kaufman and T. I. Ito in U.S. Pat. No. 4,166,071 (1979). The other type of additives are the phosphines described by C. E. Snyder, Jr. and C. Tamborski in U.S. Pat. No. 4,097,388 (1978) and C. T. Tamborski, C. E. Snyder, Jr. and J. B. Christian in U.S. Pat. No. 4,454,349 (1984). Both types of the additives exhibit some shortcomings the phospha-s-triazines are susceptible to hydrolysis whereas the phosphines exhibit limited thermal oxidative stability. This invention pertains specifically to the synthesis of hindered monophospha-s-triazines which exhibit high hydrolytic stability, as compared to previously synthesized analogues, without a decrease in their inhibition of metal corrosion and fluid degradation. These monophospha-s-triazines and the chemical intermediates employed in their preparation and disclosed herein are, to the best of our knowledge, new chemical compounds previously unknown.

SUMMARY OF THE INVENTION

It is the principal object of this invention, therefore to provide hydrolytically and thermooxidatively stable antioxidant (antidegradation) and metal/alloy corrosion inhibiting additives for perfluoroalkylether fluids.

Another object of the invention is to provide the hindered and thus hydrolytically stable monophospha-s-triazines.

A further object of the invention is to provide a process for synthesizing these monophospha-s-triazines.

Other objects and advantages of the invention will become apparent to those skilled in the art upon consideration of the accompanying disclosure.

DESCRIPTION OF THE PREFERRED EMBODIMENTS

The present invention resides in monophospha-s-triazines having the following formula:

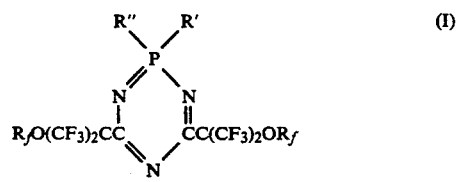

wherein $R_f$ is a perfluoroalkyl or perfluoroalkylether group and R' and R" are the same or different aryl groups. Examples of $R_f$ substituents include groups having the formula $C_nF_{2n+1}$, where n is an integer from 1 to 10, inclusive, and $C_3F_7(OCF(CF_3)CF_2)_m$, $CF_3(OCF_2CF_2)_m$, $C_2F_5(OCF_2CF_2)_m$, $C_3F_7(OCF_2CF_2CF_2)_m$, or $C_4F_9(OCF_2CF_2CF_2CF_2)_m$ where m is zero or an integer from 1 to 20 inclusive, preferably an integer from 1 to 4 inclusive. Examples of R' and R" groups include $C_6H_5$, $R$-$C_6H_4$, where R is an aromatic, alkyl, perfluoroalkyl or perfluoroalkylether and perfluoroaryl groups such as $C_6F_5$ and $R_fC_6F_4$ where $R_f$ is a perfluoroalkyl or a perfluoroalkylether group. In one embodiment, the present invention resides in a process for preparing the monophospha-s-triazine wherein $R_f = R_f'CF_2$. The synthesis procedure:

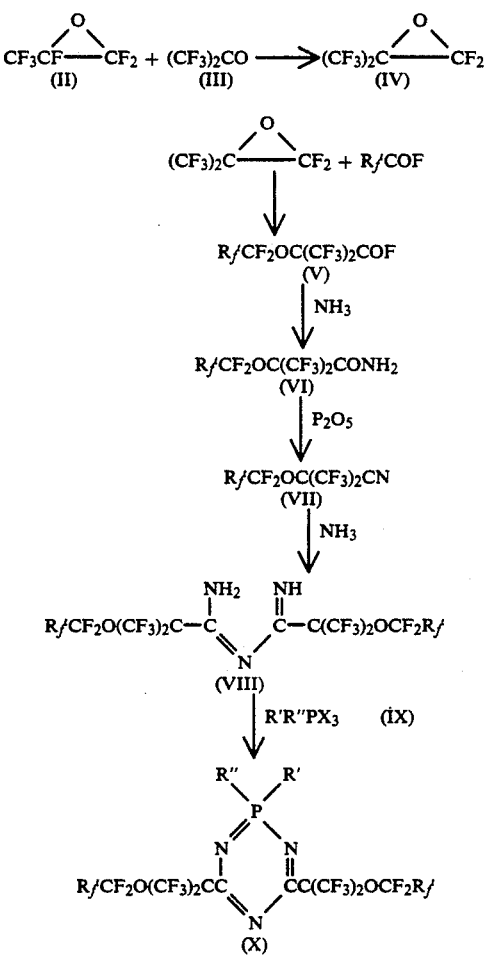

The reaction of hexafluoropropene epoxide with hexa-fluoroacetone giving the octafluoroisobutylene epoxide was described by J. T. Hill in J. Fluorine Chem., 9, 97–112 (1977). The telomerization of the epoxide with $R_f'COF$ (where $R_f'$ corresponds to $R_f$, as defined earlier, minus $CF_2$) is preferably conducted at 22 to $-11°$ C. in tetraglyme in the presence of cesium fluoride. The reaction period usually ranges from 24 to 72 hours. The reaction is carried either in vacuo or under an inert gas such as nitrogen, helium or argon. In general equimolar amounts of the reactants are utilized. The acid fluorides, $R_f'COF$, are commercially available materials. The next step is performed usually at $-78°$ to $-23°$ C. over a period of 1-24 hours. The operation is performed in an evacuated, sealed system using 2-4 mole of ammonia to one mole of the acid fluoride. The production of the nitrile, $R'CF_2OC(CF_3)_2CN$, is carried at $180°-250°$ C. under an inert gas such as nitrogen, helium or argon over a 1-6 hour period, using approximately a 10 fold excess of phosphorus pentoxide. To obtain the imidoylamidine a mixture of the nitrile described above, and ammonia in the ratio ranging from 2:1 to 1:1 is reacted at $25°-75°$ C. in an evacuated sealed ampoule. The reaction period usually ranges between 3 to 9 days although longer or shorter periods can be used. In the final step the imidoylamidine is reacted with diaryltrihalophosphorane, $R'R''PX_3$, giving the monophospha-s-triazine (I). In the foregoing example the aryl groups are defined as above while X is chlorine or bromine. During the reaction, which is conducted at temperatures ranging from 25° to 100° C., hydrogen halide is taken up by trialkylamine, usually triethylamine. The reaction is carried under an inert gas, such as nitrogen, helium or argon. The reaction period varies from 1 to 24 hours. In general equimolar quantities of the reactants are utilized, although often it is preferred to employ a small excess of the diaryltrihalophosphorane (IX). For example the mole ratio of compound IX to compound VII can vary from 1 to 1.5 to 1.

The reagents employed in the sequence leading to the hindered monophospha-s-triazine are all known; however the intermediates V, VI, VII, and VIII are all novel compositions.

A more complete understanding of the invention can be obtained by referring to the following illustrative examples which are not intended, however, to be unduly limitative of the invention.

EXAMPLE I

In vacuo a mixture of cesium fluoride (1.2 g, 7.90 mmol), tetraglyme (2.4 g) and $C_3F_7OCF(CF_3)COF$ (5.22 g, 15.72 mmol) was stirred at $-20°$ C. for 1 hour and at 0° C. also for 1 hour. Subsequently, the reaction was cooled to $-196°$ C. and octafluoroisobutylene oxide (3.39 g, 15.70 mmol) was condensed into it. Next the reaction mixture was stirred at $-22°$ C. for 17 hours and then at $-17°$ C. for 24 hours. Following this operation the volatiles were removed and fractionated in vacuo through traps cooled to 0°, $-23°$, $-47°$ and $-196°$ C. The product, $C_3F_7OCF(CF_3)CF_2OC(CF_3)_2COF$, (4.15 g, 48% yield); VP 0° C. 0.5 mmHg, (following refractionation of the 0, $-23$ and $-47$ fractions) was collected in the $-23°$ C. trap. The material was characterized by mass spectrometry in the form of its methyl ester, $C_3F_7OCF(CF_3)CF_2OC(CF_3)_2CO_2CH_3$, MS(70 eV) m/e (intensity,ion): 541 (65.8%, M-F), 491 (10.7%, M-CF_3), 375 (72.5%, $CF(CF_3)CF_2OC(CF_3)_2CO_2CH_3$), 335 (60.6%, $C_3F_7OCF(CF_3)CF_2$), 275 (46.6%, $CF_2OC(CF_3)_2CO_2CH_3$), 209 (67.3%, $C(CF_3)_2CO_2CH_3$).

EXAMPLE II

The acid fluoride, $C_3F_7OCF(CF_3)CF_2OC(CF_3)_2COF$, (4.51 g, 8.20 mmol) was reacted with ammonia (18.88 mmol) in vacuo at $-78°$ C. for 10 minutes, then at $-23°$ C. for 3 hours. The volatiles were removed at room temperature by pumping and the involatile residue was treated with dry Freon 113 (20 ml) and filtered in an inert atmosphere enclosure. The filtrate, after Freon 113 removal, gave 3.82 g (86% yeild) of $C_3F_7OCF(CF_3)CF_2OC(CF_3)_2CONH_2$ which was characterized by mass spectrometry. MS(70 eV) m/e (intensity, ion): 526 (2.1%, M-F), 360 (29.4%, M-$C_3F_7O$), 260 (7.0%, $CF_2OC(CF_3)_2CONH_2$), 194 (17.2%, C(CF_3)), 169 (25.7%, $C_3F_7$), 69 (48.4%, $CF_3$), 44 (100%, $CONH_2$), 169 (25.7%, $C_3F_7$), 69 (48.4%, $CF_3$), 44 (100%, $CONH_2$).

EXAMPLE III

A mixture of $C_3F_7OCF(CF_3)CF_2OC(CF_3)_2CONH_2$ (3.81 g, 6.90 mmol) was heated with phosphorous pentoxide (9.02 g, 63.0 mmol) under nitrogen bypass at 214° C. for 3 hours. The distillate, collected during the heating period in 0° C. cooled receiver, was purified by fractionation in vacuum through traps held at $-23°$, $-47°$, $-78°$, and $-196°$ C. The product, $C_3F_7OCF(CF_3)CF_2OC(CF_3)_2CN$, (3.42 g, 92% yield) VP 0° C., 3 mmHg collected in the $-23°$ and $-47°$ C. traps was characterized by mass spectrometry. MS(70 eV) m/e (intensity, ion): 508 (2.7%, M-F), 458 (1.4%, M-$C_2F_5$), 342 (21.1%, M-$C_3F_7O$), 242 (33.9%, $CF_2OC(CF_3)_2CN$), 192 (18.2%, $OC(CF_3)_2CN$), 176 (28.2%, $C(CF_3)_2CN$), 169 (100%, $C_3F_7$).

EXAMPLE IV

A mixture of the nitrile $C_3F_7OCF(CF_3)CF_2OC(CF_3)_2CN$ (3.36 g, 6.37 mmol) and ammonia (6.52 mmol) was heated in vacuo in a sealed ampoule at 50° C. for 6 days. The residue 3.42 g (95.4% yield), following removal of the excess of ammonia, consisted of the imidoylamidine, $C_3F_7OCF(CF_3)CF_2OC(CF_3)_2C(=NH)N=C(NH_2)C(CF_3)_2OCF_2CF(CF_3)-OC_3F_7$, based on mass balance data and infrared spectral analysis.

EXAMPLE V

To a solution of diphenyltrichlorophosphorane, $(C_6H_5)_2PCl_3$, (1.42 g, 4.87 mmol) in benzene (30 ml) heated to 50° C. was added, under nitrogen bypass, a solution of the imidoylamidine, described in the Example IV, (4.87 g, 4.55 mmol), and triethylamine (1.68 g, 16.63 mmol) in Freon 113 (30 ml) over a period of 2 hours. Stirring at 50°-55° C. under nitrogen bypass was continued for additional 18 hours. After cooling to room temperature the volatiles were removed in vacuo, the residue was redissolved in Freon 113 and filtered to remove the produced triethylamine hydrochloride. The filtrate was passed through neutral alumina column and after solvent evaporation followed by distillation at 0.001 mmHg the monophospha-s-triazine, Compound I, was obtained in 89% yield (5.08 g; GC purity>99%); MW 1200 (theory 1253). The material was characterized by its molecular weight, by infrared spectral analysis and by NMR. IR (capillary film, cm−1); 3160 (w) (aromatic CH stretching), 1570 (s) (absorption characteristic of the monophospha-s-triazine ring system), 1450 (m), 1400 (m), 1320 (sh), 1230 (vs), 1200 (m), 1160 (m), 1130 (m), 1060 (m), 1020 (w), 990 (s), 980 (sh), 930

(m), 840 (m), 810 (w), 750 (sh), 730 (m), 695 (m). $^1$H NMR, ppm (relative intensity, assignment): 7.6, 7.8 (aromatic H). $^{19}$F NMR ppm (relative intensity, assignment): −69.1, −69.8 (3.6, OC(CF$_3$)$_2$), −77.4 (1.2, CF$_3$CF$_2$CF$_2$O), −79.4 (1.7, CF$_3$CF$_2$CF$_2$O), −80.8 (3.0, OCF(CF$_3$)CF$_2$), −128.9 (1.2, CF$_3$CF$_2$CF$_2$O), −142.6 (0.6, OCF(CF$_3$)CF$_2$).

The above monophospha-s-triazine, Compound I, was found to effectively inhibit oxidation of poly(hexafluoropropene oxide) fluid (Krytox 143AC, DuPont trade name) and to prevent corrosion of Ti(4 Al, 4 Mn) alloy by the fluid. A 1% by weight solution of this monophospha-s-triazine, Compound I, decreased fluid degradation as measured by volatiles production by a factor of over 306 during a 24 hour exposure to oxygen at 316° C., as compared to an identical treatment of the fluid in the absence of the additive. These data are summarized in Table I.

TABLE 1

Degradation of Krytox Fluid in the Presence of Ti(4Al, 4Mn) Alloy Coupon at 316° C. in Oxygen for 24 Hours.$^a$

| Fluid Used g | Additive | Total Products Formed | |
|---|---|---|---|
| | | mg | mg/g$^b$ |
| 3.02 | None | 966.1 | 319.9 |
| 2.87 | 1%$^c$ Compound I | 3.0 | 1.04 |

$^a$The apparatus consisted of a sealed glass tube wherein the metal coupon was suspended in the fluid; the test was conducted in pure oxygen; at the conclusion of the test the volatile products were collected and measured.
$^b$Products formed in mg/g of Krytox employed.
$^c$The percent is weight percent of additive per weight of Krytox fluid.

The monophospha-s-triazine, Compound I, in contrast to the previously prepared monophospha-s-triazines as described by K. L. Paciorek, R. H. Kratzer, J. Kaufman and T. I. Ito in U.S. Pat. No. 4,166,071 (1979), wherein the group attached to the ring carbon atom was —CF(CF$_3$), was found to be hydrolytically stable. This is shown by the data given in Table 2.

TABLE 2

Differently Substituted Monophospha-s-triazines Hydrolysis Data.$^a$

| Ring Substituent | Weight mg | Recovered % of Phospha-s-triazineg$^b$ |
|---|---|---|
| C$_3$F$_7$[OCF(CF$_3$)CF$_2$]$_2$OCF(CF$_3$) (U.S. Pat. No. 4,166,071) | 165.3 | 3 |
| C$_3$F$_7$OCF(CF$_3$)CF$_2$OC(CF$_3$)$_2$ | 152.9 | 100 |

$^a$The tests were performed by placing the sample in 5 ml of water and heating the resulting mixture with stirring for 17 hr in oil bath kept at 104° C..
$^b$At the conclusion of the experiment the solution was extracted with Freon 113 and the residue, obtained after solvent removal, was weighted and subjected to quantitative gas chromatographic analysis.

INDUSTRIAL APPLICATION

The invention has application in the chemical process industries and in the manufacture of additives for perfluoroalkylether fluids based lubricants. The use of the hydrolytically stable additives, herein disclosed, provides for the utilization of the perfluoroalkylether lubricants at elevated temperatures or under boundary lubrication conditions in the presence of metals/metal alloys in oxidizing atmospheres for extended periods of time.

What is claimed is:

1. A monophospha-s-triazine having a general formula [R$_f$OC(CF$_3$)$_2$CN]$_2$[R'R"PN] represented by structural arrangement:

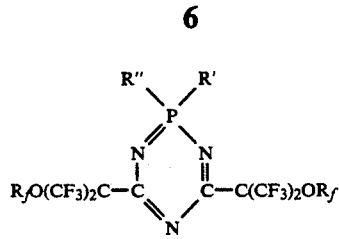

in which R$_f$ is a group having the formula C$_n$F$_{2n+1}$ where n is an integer from 1 to 10 inclusive and one or more groups selected from C$_3$F$_7$(OCF(CF$_3$)CF$_2$)$_m$, CF$_3$(OCF$_2$CF$_2$)$_m$, C$_2$F$_5$(OCF$_2$CF$_2$)$_m$, C$_3$F$_7$(OCF$_2$CF$_2$CF$_2$)$_m$ or C$_4$F$_9$(OCF$_2$CF$_2$CF$_2$CF$_2$)$_m$ where m is zero or n integer from 1 to 20 inclusive, wherein R' and R" are individually selected from the group consisting of C$_6$H$_5$ and R—C$_6$H$_4$, wherein R is an aromatic, alkyl, perfluoroalkyl or perfluoroalkylether moiety, C$_6$F$_5$ and R$_f$C$_6$F$_4$, wherein R$_f$ is a perfluoroalkyl or perfluoroalkylether moiety.

2. The monophospha-s-triazine of claim 1 wherein R$_f$ is C$_3$F$_7$OCF(CF$_3$)CF$_2$ and R' and R" are both C$_6$H$_5$.

3. A method for synthesizing the monophospha-s-triazine compound

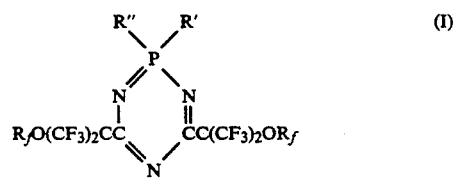

comprising the steps of:
(a) telomerizing octafluoroisobutylene epoxide with an acid fluoride of the general formula R$_f$COF wherein R$_f$ is selected from the group consisting of C$_n$F$_{2n+1}$ wherein n is an integer from 1 to 9 inclusive, C$_3$F$_7$(OCF(CF$_3$)CF$_2$)$_{m-1}$OCF(CF$_3$), CF$_3$(OCF$_2$CF$_2$)$_{m-1}$OCF$_2$, C$_2$F$_5$(OCF$_2$CF$_2$)$_{m-1}$OCF$_2$, C$_3$F$_7$(OCF$_2$CF$_2$CF$_2$)$_{m-1}$OCF$_2$CF$_2$, and C$_4$F$_9$(OCF$_2$CF$_2$CF$_2$CF$_2$)$_{m-1}$OCF$_2$CF$_2$CF$_2$, where m is zero or an integer from 1 to 20 inclusive to produce the acid fluoride R$_f$CF$_2$OC(CF$_3$)$_2$COF;
(b) reacting of the acid fluoride from step (a) with ammonia to produce R$_f$CF$_2$OC(CF$_3$)$_2$CONH$_2$;
(c) dehydrating R$_f$CF$_2$OC(CF$_3$)$_2$CONH$_2$ from step (b) with phosphorus pentoxide to produce R$_f$CF$_2$OC(CF$_3$)$_2$CN;
(d) reacting the nitrile R$_f$CF$_2$OC(CF$_3$)$_2$CN with ammonia to produce the imidoylamidine R$_f$CF$_2$OC(CF$_3$)$_2$C(=NH)N=C(NH$_2$)C(CF$_3$)$_2$OCF$_2$R$_f$
(e) condensing the R$_f$CF$_2$OC(CF$_3$)$_2$C(=NH)N=C(NH$_2$)C(CF$_3$)$_2$OCF$_2$R$_f$ from step (d) with R'R"PX$_3$, wherein R' and R" are individually selected from the group consisting of C$_6$H$_5$, R—C$_6$H$_4$, R is an aromatic, alkyl, perfluoroalkyl or perfluoroalkylether moiety, C$_6$F$_5$ and R$_f$C$_6$F$_4$, where R$_f$ is a perfluoroalkyl or perfluoroalkylether moiety, and X is either chlorine or bromine.

4. The method of claim 3 wherein the monophospha-s-triazine wherein R$_f$ is C$_3$F$_7$OCF(CF$_3$) and R' and R" are both C$_6$H$_5$.

5. The method of claim 3 wherein R$_f$ in the amide R$_f$CF$_2$OC(CF$_3$)$_2$CONH$_2$ is C$_3$F$_7$OCF(CF$_3$).

* * * * *